United States Patent
Pishdad et al.

(10) Patent No.: US 10,293,184 B2
(45) Date of Patent: May 21, 2019

(54) THERAPY CONTROL USING MOTION PREDICTION

(71) Applicant: Elekta Ltd., Montreal (CA)

(72) Inventors: Leila Pishdad, Toronto (CA); Rupert Archie Brooks, Montreal (CA)

(73) Assignee: Elekta Ltd., Montreal (CA)

( * ) Notice: Subject to any disclaimer, the term of this patent is extended or adjusted under 35 U.S.C. 154(b) by 271 days.

(21) Appl. No.: 15/387,701

(22) Filed: Dec. 22, 2016

(65) Prior Publication Data

US 2017/0216625 A1     Aug. 3, 2017

Related U.S. Application Data

(60) Provisional application No. 62/289,144, filed on Jan. 29, 2016.

(51) Int. Cl.
*A61N 5/10* (2006.01)
*A61B 6/00* (2006.01)

(52) U.S. Cl.
CPC ............ *A61N 5/1049* (2013.01); *A61B 6/541* (2013.01); *A61N 5/107* (2013.01); *A61N 5/1037* (2013.01); *A61N 5/1045* (2013.01); *A61N 5/1048* (2013.01); *A61N 5/1064* (2013.01); *A61N 2005/1052* (2013.01); *A61N 2005/1055* (2013.01); *A61N 2005/1061* (2013.01); *A61N 2005/1091* (2013.01)

(58) Field of Classification Search
CPC .. A61N 5/1037; A61N 5/1048; A61N 5/1049; A61N 5/1064; A61N 5/107
See application file for complete search history.

(56) References Cited

U.S. PATENT DOCUMENTS

| | | |
|---|---|---|
| 2008/0159478 A1 | 7/2008 | Keall |
| 2012/0253217 A1 | 10/2012 | Mostafavi |

(Continued)

FOREIGN PATENT DOCUMENTS

| | | |
|---|---|---|
| AU | 2017211683 A1 | 8/2018 |
| CN | 108883297 A | 11/2018 |
| CN | 109152926 A | 1/2019 |

(Continued)

OTHER PUBLICATIONS

International Search Report and Written Opinion from corresponding PCT Application No. PCT/IB/050427 dated Apr. 13, 2017 (7 pages).

(Continued)

*Primary Examiner* — Christine H Matthews
(74) *Attorney, Agent, or Firm* — Schwegman Lundberg & Woessner, P.A.; Sanjay Agrawal

(57) ABSTRACT

A medical system includes a medical device and a controller. The medical device is controlled according to a control protocol. The controller is configured to receive a measured data set containing a current value at a current time and past values at past times of a physiologic signal measured on a recipient, calculate a difference signal at the current time based on the measured data set, and predict a difference value using the difference signal and a prediction algorithm. The difference value is a difference between a predicted future value of the physiologic signal at a future time and the current value. The controller is further configured to calculate the predicted future value based on the difference value and the current value and update the control protocol according to the predicted future value.

20 Claims, 12 Drawing Sheets

(56) References Cited

U.S. PATENT DOCUMENTS

| | | |
|---|---|---|
| 2012/0316423 A1 | 12/2012 | Raleigh |
| 2014/0275704 A1 | 9/2014 | Zhang et al. |
| 2017/0216627 A1 | 8/2017 | Brooks et al. |

FOREIGN PATENT DOCUMENTS

| | | |
|---|---|---|
| WO | WO 2006-039009 | 4/2006 |
| WO | WO 2012-066494 | 5/2012 |
| WO | WO-2012135798 A1 | 10/2012 |
| WO | WO-2014125715 A1 | 8/2014 |
| WO | WO-2017130140 A1 | 8/2017 |
| WO | WO-2017132522 A1 | 8/2017 |

OTHER PUBLICATIONS

International Search Report and Written Opinion from PCT Application No. PCT/US2017/015358 dated Jul. 14, 2017 (18 pages).

"U.S. Appl. No. 15/387,689, Non Final Office Action dated Nov. 2, 2018", 12 pgs.

"International Application Serial No. PCT/US2017/015358, International Preliminary Report on Patentability dated Aug. 9, 2018", 10 pgs.

"U.S. Appl. No. 15/387,689, Notice of Allowance dated Jan. 25, 2019", 8 pgs.

"U.S. Appl. No. 15/387,689, Response filed Jan. 4, 2019 to Non Final Office Action dated Nov. 2, 2018", 10 pgs.

"European Application Serial No. 17743814.0, Extended European Search Report dated Jan. 17, 2019", 7 pgs.

"International Application Serial No. PCT/IB2017/050427, International Preliminary Report on Patentability dated Aug. 9, 2018", 5 pgs.

Zhendong, Luo, et al., "A reduced-order finite difference extrapolation algorithm based on POD technique for the non-stationary Navier-Stokes equations", Applied Mathematical Modelling, val. 37, No. 7, (Apr. 1, 2013), 5464-5473 pgs.

"Australian Application Serial No. 2017211332, First Examination Report dated Feb. 15, 2019", 6 pgs.

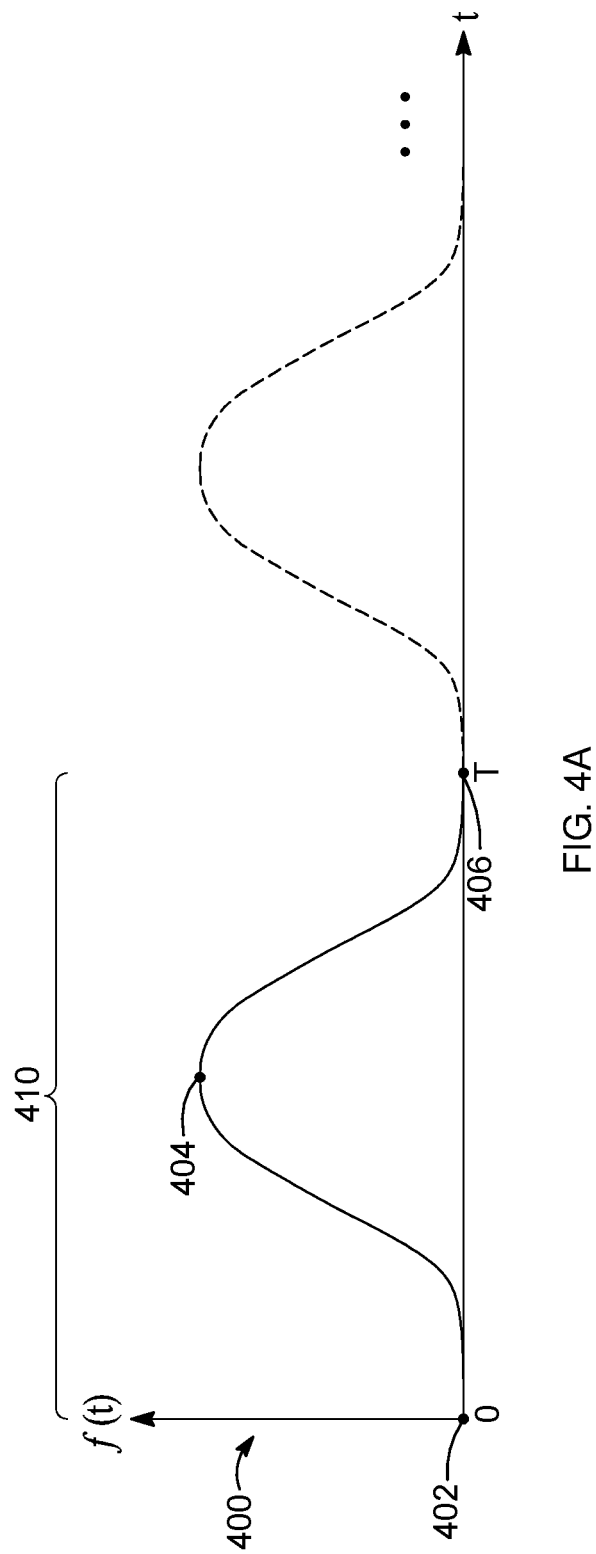

THERAPY CONTROL USING MOTION PREDICTION

CROSS-REFERENCE TO RELATED APPLICATION

This application is based upon and claims the benefit of priority from U.S. Provisional Application No. 62/289,144, filed on Jan. 29, 2016, the entire content of which is incorporated herein by reference.

TECHNOLOGY FIELD

The disclosure relates to therapy control and, more particularly, to image-guided therapy control systems and methods using motion prediction.

BACKGROUND

Radiation therapy or "radiotherapy" can be used to treat cancers or other ailments. Generally, ionizing radiation in the form of a collimated beam is directed from an external source toward a patient. The dose of an applied radiation therapy beam or a sequence of applied radiation therapy beams is generally controlled such that a target locus within the patient, such as a tumor, receives a prescribed cumulative dose of radiation, while radiation-induced damage to healthy tissue surrounding the target locus is to be avoided. The radiation therapy beam can include high-energy photons, electrons, or other particles such as protons.

In one approach, a radiation therapy beam can be generated, for example, at least in part using a linear accelerator. The linear accelerator accelerates electrons and directs the electrons to a target, such as a metallic target, to elicit high-energy photons. The high-energy photons, generally having an energy in a mega-electron-volt (MeV) range for therapeutic use, can then be controlled, shaped, or modulated and directed to the target locus, such as a tumor region within the patient. A specified or selectable therapy beam energy can be used, such as for delivering a diagnostic energy level range or a therapeutic energy level range. Modulation of a therapy beam can be provided by one or more attenuators or collimators. The field size and shape of the radiation beam can be adjusted to avoid damaging healthy tissue adjacent to the targeted tissue by conforming the projected beam to a profile of the targeted tissue.

In one approach, a treatment plan can be developed before radiation therapy is delivered, such as using one or more medical imaging techniques. In such an approach, imaging can be performed in an "offline" manner. A health care provider, such as a physician, may use three-dimensional imaging information indicative of the patient anatomy to identify a target locus along with other regions such as organs near the tumor. Such imaging information can be obtained using various imaging modalities, such as X-ray, computed tomography (CT), magnetic resonance imaging (MRI), positron emission tomography (PET), or single-photon emission computed tomography (SPECT), etc. The health care provider can delineate the target locus that is to receive a prescribed radiation dose using a manual technique, and the health care provider can similarly delineate nearby tissue, such as organs, at risk of damage from the radiation treatment. Alternatively or additionally, an automated tool can be used to assist in identifying or delineating the target locus. A radiation therapy treatment plan can then be created based on clinical or dosimetric objectives and constraints. The treatment plan can then be executed by positioning the patient and delivering the prescribed radiation therapy to the patient. The therapy treatment plan can include dose "fractioning," whereby a sequence of radiation therapy deliveries are provided, with each therapy delivery including a specified fraction of a total prescribed dose.

As discussed above, a radiation therapy can be guided by images that provide knowledge of the target locus. However, certain anatomical regions, e.g., the lungs, are subject to quasiperiodic motion such as respiratory motion, that is significant enough to affect the treatment. For example, respiratory motion may change the locations of some organs, such as thoracic or abdominal organs. The movement of the organ caused by the respiratory motion can lead to imaging artifacts, making the images less effective in guiding the therapy. Therefore, further knowledge of the respiratory motion may be needed to plan an effective radiation therapy. However, unlike periodic motion, quasiperiodic motion does not have a fixed frequency, making it harder to predict future motions.

Moreover, the respiratory motion typically occurs for a relatively short time period. However, the process of taking an image, analyzing it, and determining the position of the target, can take a long time. That results in a latency between acquiring the mage and compensating for the respiratory motion. Therefore, the prediction of the respiratory motion is needed to allow a prediction of the target position in real time.

The disclosed methods and systems are designed to further improve the motion prediction.

SUMMARY

In accordance with the present disclosure, there is provided a medical system including a medical device and a controller. The medical device is controlled according to a control protocol. The controller is configured to receive a measured data set containing a current value at a current time and past values at past times of a physiologic signal measured on a recipient and calculate a difference signal at the current time based on the measured data set. The difference signal includes a first order finite difference of the physiologic signal at the current time and a second order finite difference of the physiologic signal at the current time. The controller is also configured to predict a difference value using the difference signal and a prediction algorithm. The difference value is a difference between a predicted future value of the physiologic signal at a future time and the current value. The controller is further configured to calculate the predicted future value based on the difference value and the current value and update the control protocol according to the predicted future value.

Also in accordance with the present disclosure, there is provided a method for controlling a medical device. The method includes receiving a measured data set containing a current value at a current time and past values at past times of a physiologic signal measured on a recipient and calculating a difference signal at the current time based on the measured data set. The difference signal includes a first order finite difference of the physiologic signal at the current time and a second order finite difference of the physiologic signal at the current time. The method also includes predicting a difference value using the difference signal and a prediction algorithm. The difference value is a difference between a predicted future value of the physiologic signal at a future time and the current value. The method further includes calculating the predicted future value based on the difference value and the current value and updating a control protocol of the medical device according to the predicted future value. The control protocol controls the medical device.

Features and advantages consistent with the disclosure will be set forth in part in the description which follows, and in part will be obvious from the description, or may be learned by practice of the disclosure. Such features and advantages will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF DRAWING

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 4A illustrates a one-dimensional representation of an exemplary cyclic motion model, corresponding to a respiration cycle.

DETAILED DESCRIPTION

Figure 1A:
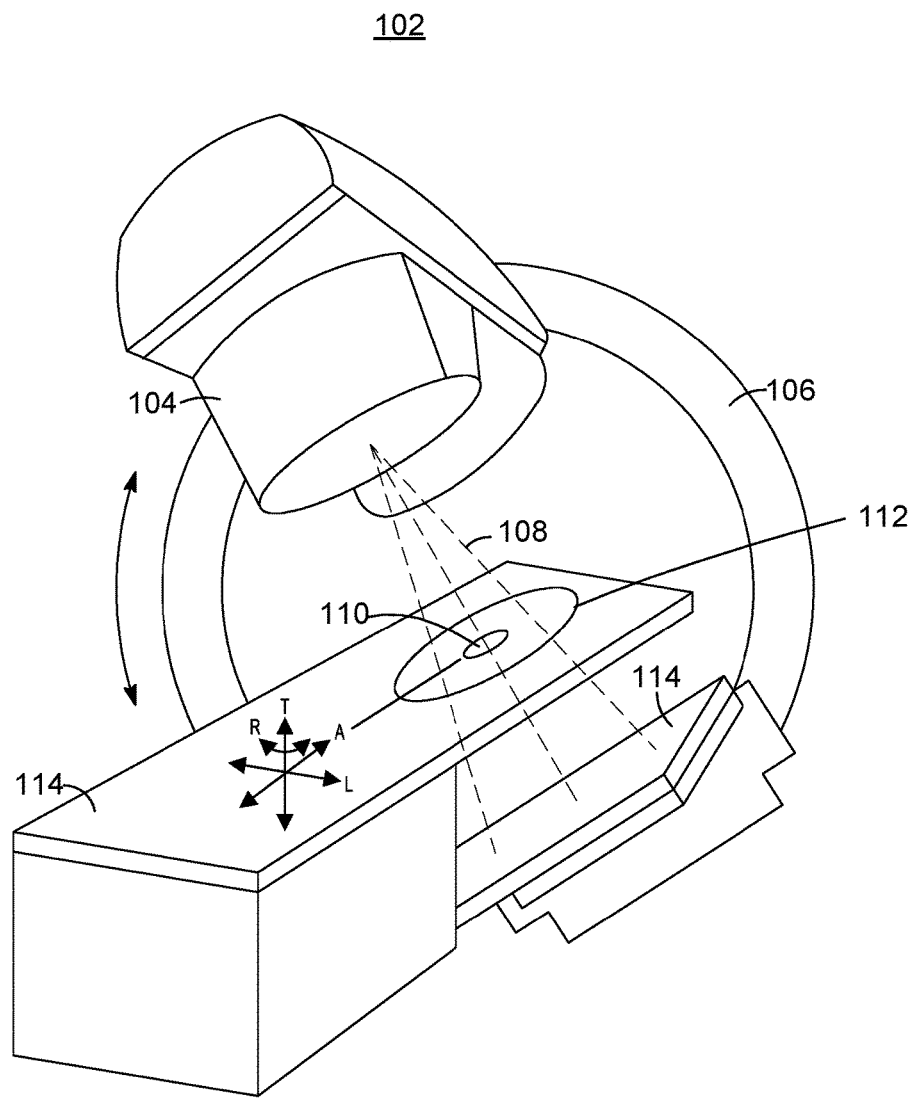
FIG. 1A illustrates an exemplary radiation therapy system that can include radiation therapy output configured to provide a therapy beam.

A radiation therapy treatment plan can be adjusted contemporaneously with therapy delivery in an adaptive manner, such as to compensate for cyclical changes in a position of a target locus to be treated with a radiation therapy. For example, a desired target, such as a tumor or an organ at risk, can shift in position to such an extent that if an exclusively "offline" approach to therapy planning is used, a therapy locus of delivered radiation therapy can become misaligned with the desired target when the radiation therapy is eventually delivered.

In one exemplary approach, imaging can be performed contemporaneously with delivery of a radiation therapy, such as performing an imaging acquisition just before initiating radiation therapy delivery during a therapy delivery session, or using a sequence of respective therapy delivery and imaging acquisition instances over a course of a radiation therapy delivery session. Such imaging can provide information helpful for identifying a position of the target locus or for identifying motion of the target locus. Such contemporaneous imaging can be referred to generally as "real-time," although a latency or time delay usually exists between an acquisition of an image and a delivery of radiation therapy.

Motion of the target locus can be caused by one or more sources, such as heart motion, respiration, a reflex such as a cough, or other movements. In the case of cyclic motion, such as associated with respiration, a trajectory of a target locus can be predicted using a cyclic motion model along with imaging information obtained regarding earlier motion of the target locus. For example, a predicted target locus for an upcoming time of therapy delivery can be generated using information indicative of an earlier target locus extracted from the imaging information, along with a cyclic motion model, according to a specified latency between image acquisition of the earlier target locus and the scheduled upcoming time of therapy delivery.

An updated therapy protocol can be generated in an adaptive manner to align the therapy locus with the predicted target locus. A therapy protocol is generally a therapy plan that the therapy delivery system may execute. For example, the therapy protocol can include one or more of: (a) adjustment of one or more of actuators coupled to a moveable platform such as a couch or table supporting the therapy recipient, (b) adjustment of one or more apertures configured to collimate or shape the therapy beam, or (c) adjustment of one or more actuators configured to position a therapy output to establish a specified therapy beam direction. Such adjustment can be performed automatically before or during therapy delivery. The adjustments may be characterized using parameter values, trajectories, ranges, etc. Updating a therapy protocol may involve updating such values, trajectories, or ranges.

In an illustrative example, the cyclic motion model can be established at least in part using a series of two or more imaging acquisitions, such as acquisitions of three-dimensional (volumetric) imaging information of a region. Later, such as just before therapy delivery, the time-varying target locus within the therapy recipient can be established using other imaging information after establishing the cyclic motion model. Such other imaging information can include one or more of two-dimensional imaging or volumetric imaging slices including a sub-region within the prior-imaged volumetric region. For example, a predicted target locus can be automatically generated by extracting information indicative of a feature from two-dimensional imaging information or imaging slices, the feature corresponding to an earlier target locus. A phase of the cyclic motion model corresponding to the location of the feature can be determined. In response to determining the phase, a change in the location of the feature can be predicted using a later phase of the cyclic motion model corresponding to the scheduled upcoming time of therapy delivery can be determined. For example, a spatial displacement in the location of the feature can be predicted using a difference in outputs of the cyclic motion model between the earlier phase and later phases.

The information indicative of the determined change in the location of the feature can be applied to the information indicative to the earlier target locus to provide the predicted target locus. For example, a spatial displacement of the feature can be applied to the information indicative of the earlier target locus, such as shifting a centroid of the earlier target locus to obtain a predicted target locus. The target locus can include a tumor, and shifting the location of the earlier target locus to obtain the predicted target locus can include assuming that the locus is rigid (e.g., assuming that the predicted target locus is not deformed as compared to the earlier target locus).

According to various illustrative examples described in this document, apparatus and techniques described herein can include use of a linear accelerator (LINAC) to generate a radiation therapy beam, and use of one or more of a computed tomography (CT) imaging system, or a nuclear magnetic resonance (MR) imaging system to acquire the imaging information. Other imaging modalities and radiation therapy techniques can be used.

It is contemplated that a radiotherapy delivery system is just one example of a medical system, and a therapy protocol is one example of a control protocol, according to which a medical system can be controlled. "A medical system," consistent with the disclosure, may include any medical device that measures patient data that is affected by motions. Such a medical system may be a treatment system, a surgical system, a monitoring system, or a diagnostic system. The motions may be quasiperiodic, such as cardiac motions and respiratory motions. A "control protocol" may be used to control the operation of a medical system, in a way that compensates for the motions. For example, a control protocol may include adjustments of any components of the particular medical system being controlled.

FIG. 1A illustrates an exemplary radiation therapy system 102 that can include radiation therapy output 104 configured to provide a therapy beam 108. The radiation therapy output 104 can include one or more attenuators or collimators, such as a multi-leaf collimator (MLC) as described in the illustrative example of FIG. 2. Referring back to FIG. 1A, a patient can be positioned in a region 112, such as on a platform 116 (e.g., a table or a couch), to receive a radiation therapy dose according to a radiation therapy treatment plan. The radiation therapy output 104 can be located on a gantry 106 or other mechanical support, such as to rotate the therapy output 104 around an axis ("A"). One or more of the platform 116 or the radiation therapy output 104 can be moveable to other locations, such as moveable in transverse direction ("T") or a lateral direction ("L"). Other degrees of freedom are possible, such as rotation about one or more other axes, such as rotation about a transverse axis (indicated as "R").

The coordinate system (including axes A, T, and L) shown in FIG. 1A can have an origin located at an isocenter 110. The isocenter can be defined as a location where the radiation therapy beam 108 intersects the origin of a coordinate axis, such as to deliver a prescribed radiation dose to a location on or within a patient. For example, the isocenter 110 can be defined as a location where the radiation therapy beam 108 intersects the patient for various rotational positions of the radiation therapy output 104 as positioned by the gantry 106 around the axis A.

In an example, a detector 114 can be located within a field of the therapy beam 108, such as can include a flat panel detector (e.g., a direct detector or a scintillator detector). The detector 114 can be mounted on the gantry 106 opposite the radiation therapy output 104, such as to maintain alignment with the therapy beam 108 as the gantry 106 rotates. In this manner, the detector 114 can be used to monitor the therapy beam 108 or the detector can be used 114 for imaging, such as portal imaging.

In some embodiments, therapy beam 108 may be a kilovolts (KV) beam or a megavolts (MV) beam. Therapy beam 108 may be made up of a spectrum of energies, the maximum energy of which is approximately equal to the beam's maximum electric potential times the electron charge. For an MV beam, the maximum electric potential used by the linear accelerator to produce the photon beam is on the megavolts level. For example, a 1 MV beam will produce photons of no more than about 1 megaelectron-Volt (MeV).

In an illustrative example, one or more of the platform 116, the therapy output 104, or the gantry 106 can be automatically positioned, and the therapy output 104 can establish the therapy beam 108 according to a specified dose for a particular therapy delivery instance. A sequence of therapy deliveries can be specified according to a radiation therapy treatment plan, such as using one or more different orientations or locations of the gantry 106, platform 116, or therapy output 104. The therapy deliveries can occur sequentially, but can intersect in a desired therapy locus on or within the patient, such as at the isocenter 110. A prescribed cumulative dose of radiation therapy can thereby be delivered to the therapy locus while damage to tissue nearby the therapy locus is reduced or avoided.

Figure 1B:
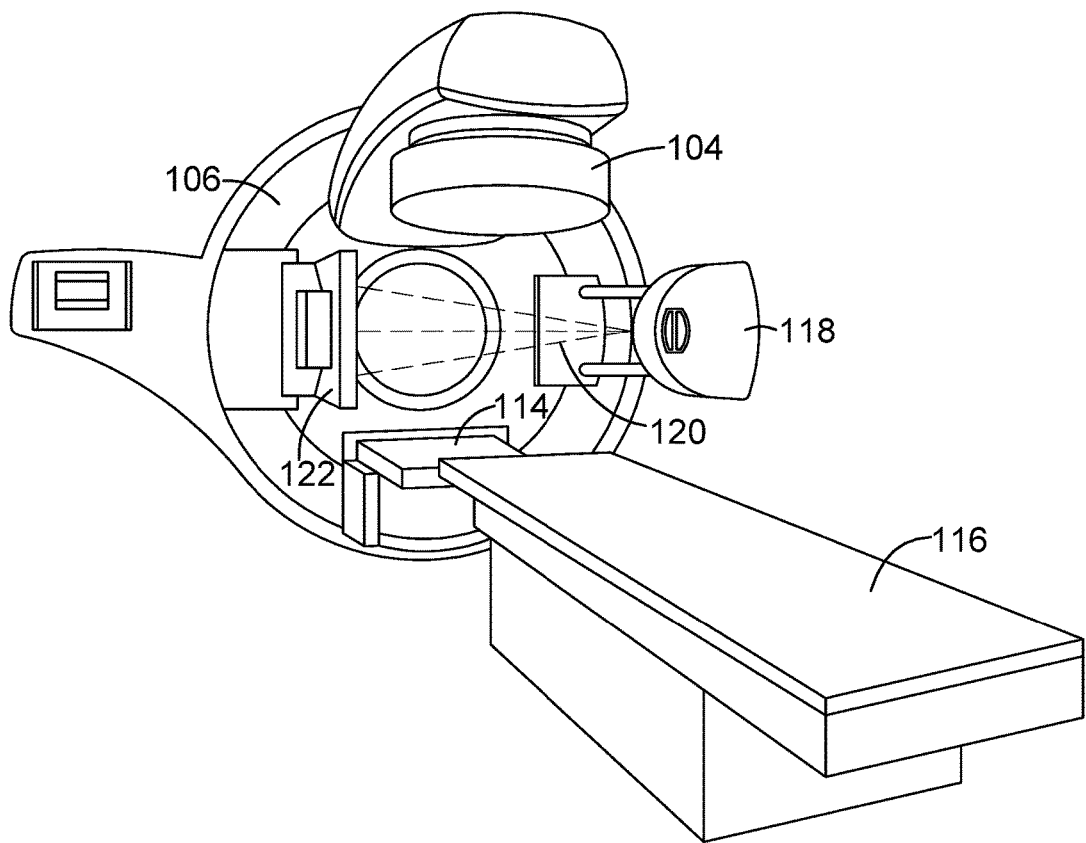
FIG. 1B illustrates an exemplary system including a combined radiation therapy system and an imaging system, such as a computed tomography (CT) imaging system.

FIG. 1B illustrates an exemplary system that can include a combined radiation therapy system 102 and an imaging system, such as can include a computed tomography (CT) imaging system. The CT imaging system can include an imaging X-ray source 118, such as providing X-ray energy in a kiloelectron-Volt (keV) energy range or a megaelectron-Volt (MeV) range. The imaging X-ray source 118 provide a fan-shaped and/or a conical beam 120 directed to an imaging detector 122, such as a flat panel detector. The radiation therapy system 102 can be similar to the system 102 described in relation to FIG. 1A, such as including a radiation therapy output 104, a gantry 106, a platform 116, and another flat panel detector 114. As in the examples of FIG. 1A and FIG. 1C, the radiation therapy system 102 can be coupled to, or can include, a high-energy accelerator configured to provide a therapeutic radiation beam. The X-ray source 118 can provide a comparatively-lower-energy X-ray diagnostic beam, for imaging.

In the illustrative example of FIG. 1B, the radiation therapy output 104 and the X-ray source 118 can be mounted on the same rotating gantry 106, rotationally-separated from each other by 90 degrees. In another example, two or more X-ray sources can be mounted along the circumference of the gantry 106, such as each having its own detector arrangement to provide multiple angles of diagnostic imaging concurrently. Similarly, multiple radiation therapy outputs 104 can be provided.

Figure 1C:
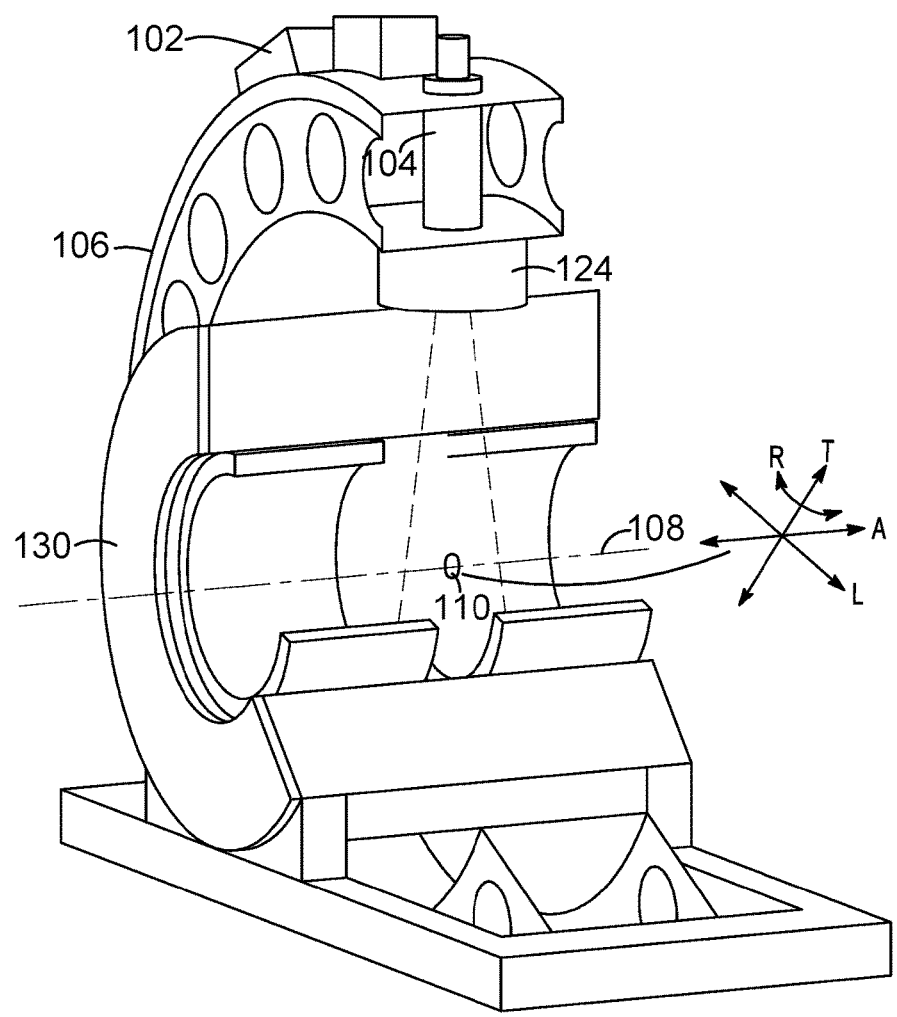
FIG. 1C illustrates a partially cut-away view of an exemplary system including a combined radiation therapy system and an imaging system, such as a nuclear magnetic resonance (MR) imaging system.

FIG. 1C illustrates a partially cut-away view of an exemplary system that can include a combined radiation therapy system 102 and an imaging system, such as can include a nuclear magnetic resonance (MR) imaging system 130. The MR imaging system 130 can be arranged to define a "bore" around an axis ("A"), and the radiation therapy system can include a radiation therapy output 104, such as to provide a radiation therapy beam 108 directed to an isocenter 110 within the bore along the axis, A. The radiation therapy output 104 can include a collimator 124, such as to one or more of control, shape, or modulate radiation therapy beam 108 to direct the beam 108 to a therapy locus aligned with a desired target locus within a patient. The patient can be supported by a platform. The platform can be positioned along one or more of an axial direction, A, a lateral direction, L, or a transverse direction, T. One or more portions of the radiation therapy system 102 can be mounted on a gantry 106, such as to rotate the radiation therapy output 104 about the axis A.

FIG. 1A, FIG. 1B, and FIG. 1C illustrate examples including a configuration where a therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient.

Figure 2:
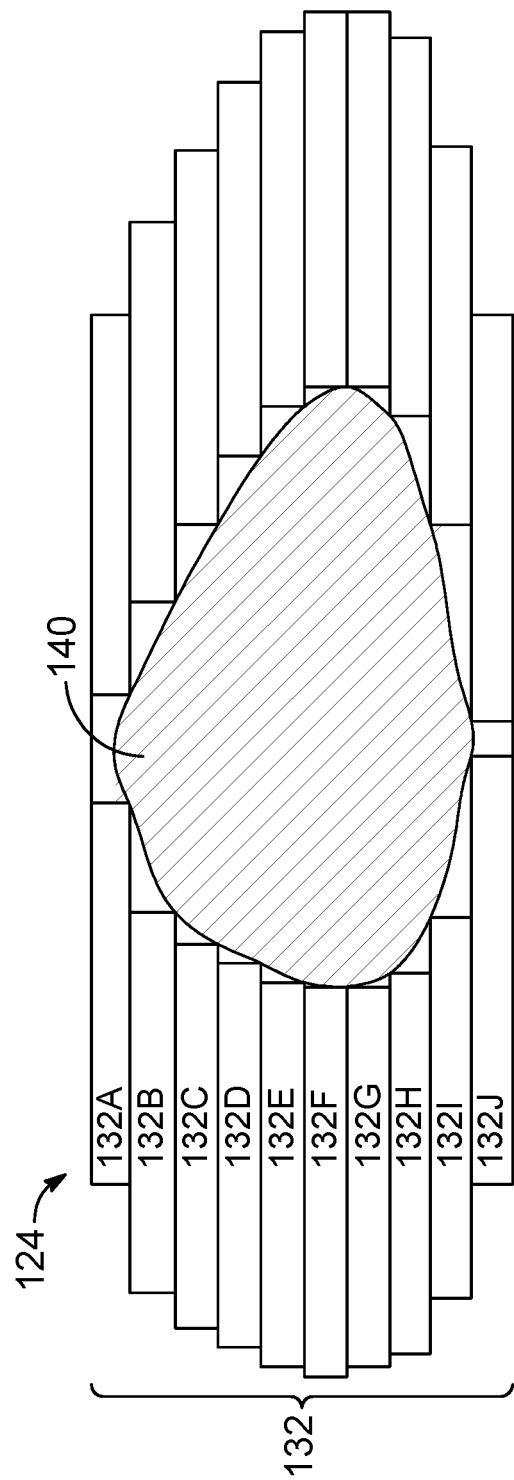
FIG. 2 illustrates an exemplary collimator configuration for shaping, directing, or modulating an intensity of a radiation therapy beam.

FIG. 2 illustrates an exemplary multi-leaf collimator (MLC) 132, for shaping, directing, or modulating an intensity of a radiation therapy beam. In FIG. 2, leaves 132A through 132J can be automatically positioned to define an aperture approximating a tumor 140 cross section or projection. The leaves 132A through 132J can be made of a material specified to attenuate or block the radiation beam in regions other than the aperture, in accordance with the radiation treatment plan. For example, the leaves 132A through 132J can include metallic plates, such as comprising tungsten, with a long axis of the plates oriented parallel to a beam direction, and having ends oriented orthogonally to the beam direction (as shown in the plane of the illustration of FIG. 2). A "state" of the MLC 132 can be adjusted adaptively during a course of radiation therapy, such as to establish a therapy beam that better approximates a shape or location of the tumor 140 or other target locus, as compared to using a static collimator configuration or as compared to using an MLC 132 configuration determined exclusively using an "offline" therapy planning technique. A radiation therapy technique using the MLC 132 to produce a specified radiation dose distribution to a tumor or to specific areas within a tumor can be referred to as Intensity Modulated Radiation Therapy (IMRT).

Figure 3A:
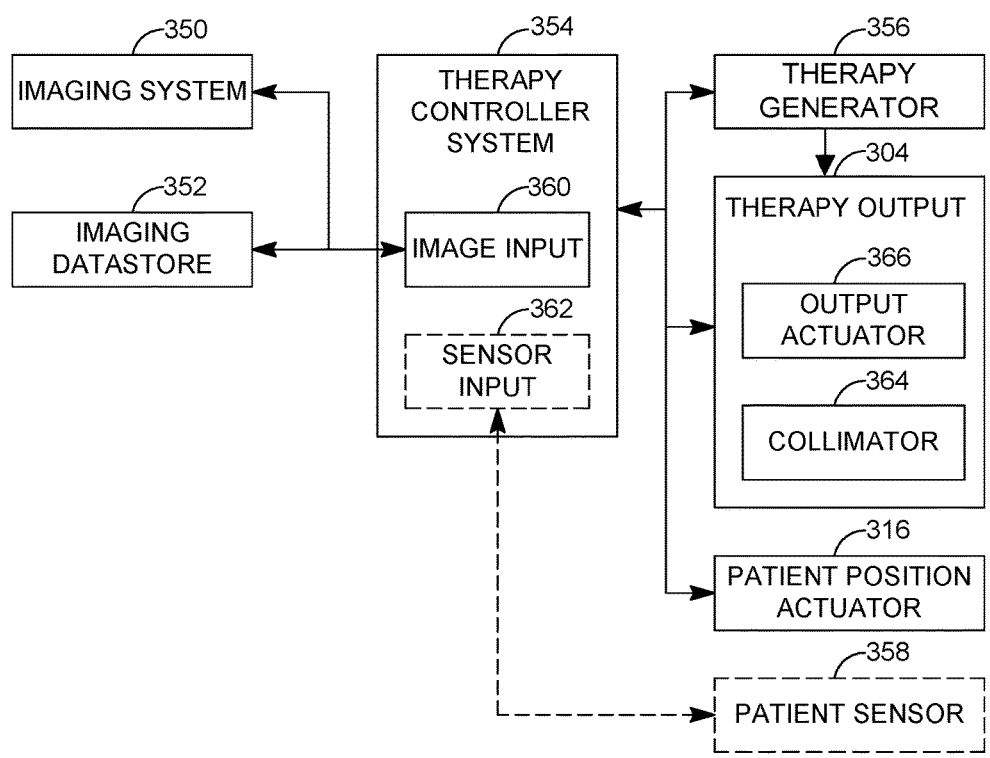
FIG. 3A illustrates an exemplary system including a radiation therapy controller having an imaging input, a radiation therapy generator, and a radiation therapy output.

FIG. 3A illustrates an exemplary system 300 including a radiation therapy controller system 354 having an imaging input 360, a radiation therapy generator 356, and a radiation therapy output 304. The therapy generator 356 can include an accelerator, such as a linear accelerator, and the therapy output 304 can be coupled to the therapy generator 356 to process a beam of energetic photons or particles provided by the therapy generator 356. For example, the therapy output 304 can include or can be coupled to an output actuator 366 to one or more of rotate or translate the therapy output 304 to provide a radiation therapy beam having a therapy locus directed to a desired target locus. The therapy output 304 can include a collimator 364, such as a multi-leaf collimator as mentioned above in relation to FIG. 2. Referring back to FIG. 3A, the therapy controller system 354 can be configured to control one or more of the therapy generator 356, the therapy output 304, or a patient position actuator 316 (such as a movable platform including a couch or table), using an adaptive radiation treatment technique as described in other examples herein.

The therapy controller system 354 can be coupled to one or more sensors, such as using a sensor input 362. For example, a patient sensor 358 can provide physiologic information to the therapy controller system, such as information indicative of one or more of respiration (e.g., using a plethysmographic sensor), patient cardiac mechanical or electrical activity, peripheral circulatory activity, patient position, or patient motion. Such information can provide a surrogate signal correlated with motion of one or more organs or other regions to be targeted by the therapy output 304.

The imaging input 360 can be coupled to an imaging system 350 (such as can include a computed tomography imaging system or a nuclear magnetic resonance (MR) imaging system, as illustrative examples). Alternatively, or in addition, the therapy controller system 354 can receive imaging information from an imaging data store 352, such as a centralized imaging database or imaging server. One or more of the therapy controller system 354 or the imaging system 350 can include elements shown and described in relation to the system 396 shown in FIG. 3B.

Figure 3B:
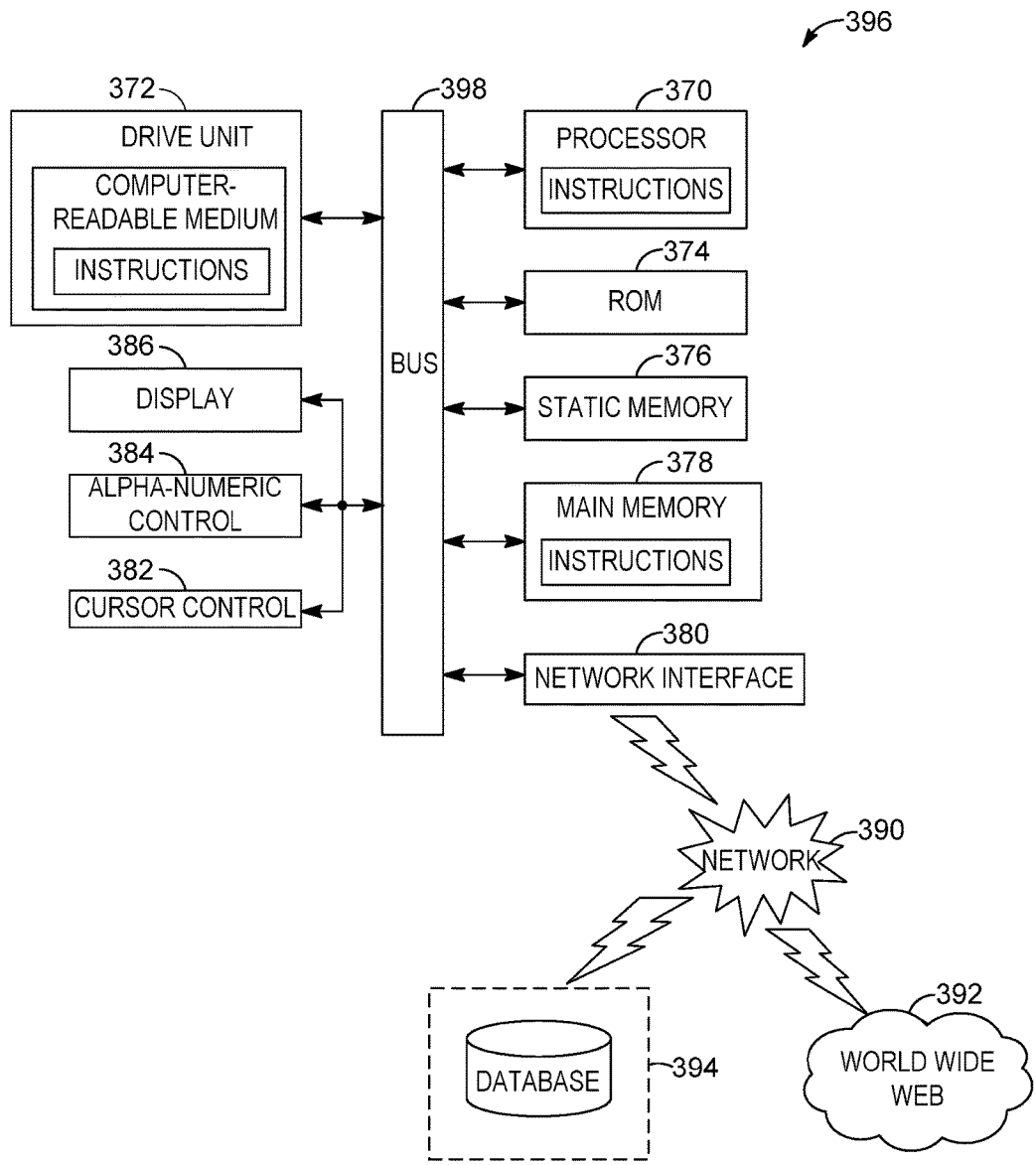
FIG. 3B illustrates a portion of an exemplary system included in a radiation therapy controller system or an imaging system.

FIG. 3B illustrates a portion of a system 396 including elements of a radiation therapy controller system 354 or an imaging system 350. The system 396 can include a main memory circuit 378 into which executable instructions or other data can be loaded, and a processor circuit 370 to execute or otherwise perform such instructions. The system 396 can include a static memory circuit 376, such as to provide a cache or other structure to store data related to a currently-executing series of instructions. A read-only memory (ROM) circuit 374 can permanently store instructions such as to facilitate a boot sequence for the system 396 or to facilitate operation of hardware devices attached to the system 396.

The system 396 can include a bus circuit 398 configured to convey information between elements or circuits comprising the system 396. For example, a drive unit 372 can be included or attached to the server, such as to store instructions related to the radiation therapy planning, imaging, or radiation therapy delivery techniques as mentioned elsewhere herein. The system 396 can include one or more of a display 386 such as can include a bit-field or alphanumeric display, an alphanumeric control 384 such as a keyboard, or a cursor control device 382 such as a touch screen, touch pad, trackball, or mouse. Examples of systems that can use or include elements of the system 396 include one or more of the therapy controller system 354, the imaging system 350, or a treatment planning system.

The system 396 can be connected to a centralized network 390 (e.g., a local area network, an "intranet," or a wide area network such as the Internet), such as to store or retrieve information from a server 394 (e.g., such as a server housing an imaging information database, a radiation therapy treatment plan, or other information such as a patient medical record). For example, the system 396 can include one or more wired or wireless interface circuits, such as a network interface circuit 380 configured to provide access to other systems such as to facilitate exchange of imaging or radiation therapy control information.

The system 396 can describe an embedded controller included as a portion of other apparatus, a personal computer (PC), a tablet device, or a cellular communications device such as a "smart" cellular device, as illustrative examples. While a single processor circuit 370 is shown illustratively in FIG. 3B, a plurality of processor circuits, "cores," or machines can be used, such as can individually or jointly perform a set (or multiple sets) of instructions to perform any one or more of the techniques described herein, such as instructions stored on a processor-readable medium (also referred to as a computer-readable medium).

Illustrative examples of a processor-readable medium include solid-state memories, optical, or magnetic media. For example, solid-state memories can include one or more of a read-only memory (ROM), a flash memory, a dynamic random access memory (DRAM) such as synchronous DRAM (SDRAM) or Rambus DRAM (RDRAM and the like)), or a static memory (e.g., flash memory, static random access memory (SRAM, or the like)).

The processor circuit 370 can include one or more processing circuits such as a microprocessor, a central processing unit, or the like. In particular, the processor can include a complex instruction set computing (CISC) architecture microprocessor, a reduced instruction set computing (RISC) architecture microprocessor, or a very long instruction word (VLIW) architecture microprocessor. According to other examples, the processor circuit 370 can include one or more of a microcontroller, an application specific integrated circuit (ASIC), a field programmable gate array (FPGA), a digital signal processor (DSP), a network processor, or a system-on-chip (SoC) circuit. For example, a microcontroller can include one more integrated circuits having a memory circuit and processor circuit co-integrated within a single device package.

Motion Prediction for Adaptive Radiation Therapy Using Imaging and a Cyclic Motion Model As mentioned above, a radiation therapy treatment plan can be adjusted contemporaneously with therapy delivery in an adaptive manner, such as to compensate for cyclical changes in a position of a target locus to be treated with a radiation therapy. For example, a desired target, such as a tumor, can shift in position to such an extent that if an exclusively "offline" approach to therapy planning is used, a therapy locus of delivered radiation therapy can become significantly misaligned with the desired target when the radiation therapy is eventually delivered. Motion of the target locus can be caused by one or more sources, such as heart motion, respiration, a reflex such as a cough, or other movements. In the case of cyclic motion, such as associated with respiration, a trajectory of a target locus can be predicted using a cyclic motion model along with imaging information obtained regarding earlier motion of the target locus. The techniques described below can be implemented in whole or in part using, or can use, the systems described above in relation to one or more of FIG. 1A, FIG. 1B, FIG. 1C, FIG. 2, FIG. 3A, or FIG. 3B.

FIG. 4A illustrates a one-dimensional representation of a cyclic motion model 400, corresponding to physiologic cycle 410 (e.g., a respiration cycle), such as defined over a duration extending from a time, 0, to time "T," where T represents a period of the cyclic motion. The motion model 400 can represent an absolute or relative spatial position or displacement, such as modeling an absolute or relative trajectory of an organ as function of time, $f(t)$. The trajectory can represent time-varying motion of a feature corresponding to the organ. In some embodiments, the feature can be a reliably-identifiable point on the organ, such as a centroid of the organ. In an illustrative example where the cyclic motion model represents respiration, at time "0" the function $f(0)$ can define a beginning-of-inspiration (BOI) reference datum 402. The function also defines an end-of-inspiration (EOI) or beginning-of-expiration (BOE) reference datum 404. At time T, the function $f(T)$ can define an end-of-expiration (EOE) datum 406.

In the illustrative example of FIG. 4A, the motion model $f(t)$ is shown as a scalar function of time having a single displacement dimension. However, such a model is merely illustrative and other examples can include a cyclic motion model defined by multiple spatial displacement functions. For example, in a Cartesian coordinate system, such spatial displacement functions comprising the cyclic motion model can be represented by functions $x(t)$, $y(t)$, and $z(t)$. One or more of the reference locations (e.g., BOI, EOI, BOE, EOE) defined in FIG. 4A can be defined within one or more of $x(t)$, $y(t)$, and $z(t)$. Accordingly, the cyclic motion model can be developed for each dimensional component. While various examples herein refer generally to continuous time mathematical functions, an automated implementation of techniques described herein can include using a discretized representation of the cyclic motion model (e.g., a sampled or discrete representation of the model values corresponding to discrete time or discrete phase values).

Figure 4B:
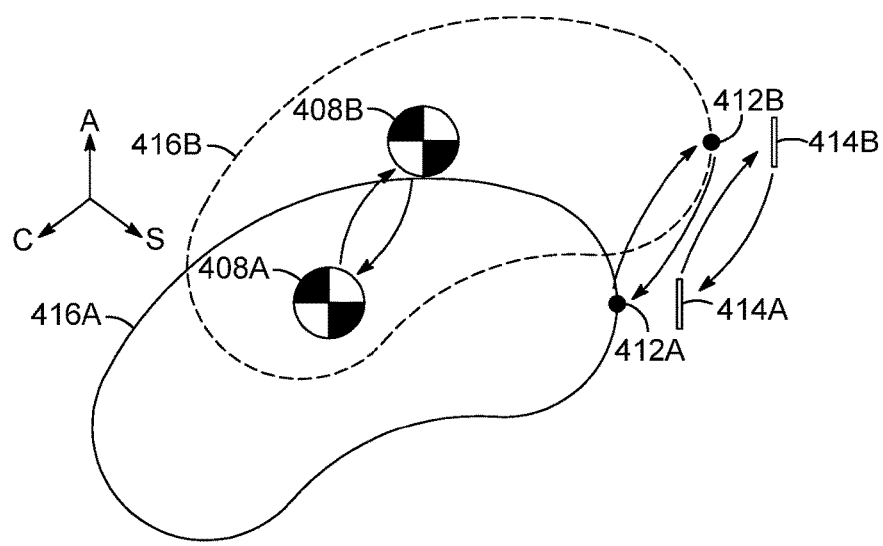
FIG. 4B illustrates an exemplary cyclic motion of a region of interest including a tumor.

FIG. 4B illustrates a cyclic motion of a region of interest 416A. According to various embodiments, the region of interest 416A can include an organ, a portion of an organ, or a tumor. A series of two or more imaging acquisitions can be performed, using one or more imaging techniques to obtain imaging information representative of the location of the region of interest 416A. For example, one or more of computed tomography (CT) or nuclear magnetic resonance (MR) imaging can be used, such as in an "offline" manner, to establish a location of the region of interest 416A.

The location of the region of interest 416A can be established from the imaging information at least in part using one or more of manual delineation of a boundary of the region of interest 416A, or an automated segmentation technique. For example, segmentation can include assigning one or more pixels or voxels from acquired imaging information as being members of the set corresponding to the region of interest 416A. Segmentation can include determining a contrast value of one or more pixels or voxels and comparing the contrast value to a criterion (e.g., a contrast threshold), such as to assist group the one or more pixels or voxels as members of the set containing the region of interest. A feature can then be extracted from the segmented region of interest 416A, such as a centroid location 408A.

The region of interest 416A can move in a time-varying fashion, such as to a location corresponding to a displaced region of interest 416B, having a correspondingly-displaced centroid 408B. Information about a displaced region of interest 416B and the correspondingly-displaced centroid 408B can also be extracted from one or more images in the series of two or more imaging acquisitions mentioned above. In this manner, a series of two or more images can be used to describe an absolute or relative trajectory of a feature, such as the determined centroid 408A and centroid 408B locations. In an illustrative example, the series of two or more images comprises a series of volumetric images (e.g., a "4D" series of images including three spatial dimensions acquired at different times). Other types of imaging can be used, such as one-dimensional imaging, or two-dimensional imaging or imaging slices extending in two dimension and also having a finite depth.

The use of a centroid as an extracted feature is illustrative. Other features can be used, such as a manually-identified or automatically-determined location of a point or surface (e.g., an edge 412A of the region-of-interest 416A and a displaced edge 412B of the displaced region of interest 416B). In yet another example, a motion of an implantable or external seed fiducial can be tracked, such using a motion of an indicium 414A (that can represent a seed location at a first time) in the imaging information corresponding to a first location, and a displaced indicium 414B corresponding to the displaced location (that can represent the seed location at a later time). Other techniques can be used to track displacement, such as use of an MR imaging "navigator echo," such as assigned to a location near an edge of an anatomical feature nearby or included as a portion of the region of interest.

Figure 5:
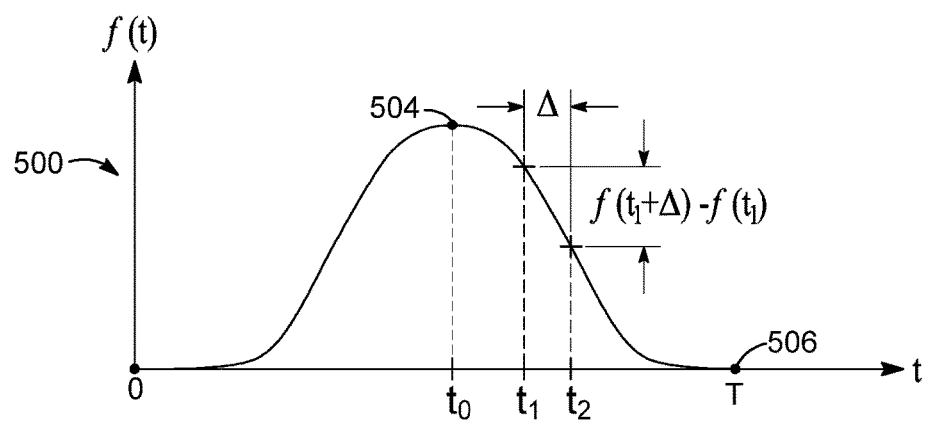
FIG. 5 illustrates an example for using a cyclic motion model to predict a target locus using information indicative of an earlier target locus extracted from imaging information.

FIG. 5 illustrates an exemplary cyclic motion model 500 to predict a target locus using information indicative of an earlier target locus extracted from imaging information. Imaging information can be obtained contemporaneously with radiation therapy delivery, such as to adjust a radiation therapy protocol to adaptively compensate for motion of a radiation therapy target locus. For example, imaging information can be obtained just before therapy delivery to be used in determining a predicted target locus. Information about one or more acquired images can be used to align an instance of an imaging acquisition with a portion of the cyclic motion model, such as including determining a relative time between a reference datum such as a datum 504 (corresponding to a time $t_0$), and a time, $t_1$, corresponding to an acquired image instance. In the illustrative example of a respiration model, the datum 504 can correspond to an end of inspiration (EOI) or a beginning of expiration (BOE) and can be detected such as by analyzing a gradient of respiration-related information from information extracted from a series of images corresponding to a complete respiratory cycle, or using surrogate information obtained from another sensor (e.g., a plethysmographic sensor).

A scheduled upcoming therapy delivery time can occur at $t_2$. Accordingly, a predicted target location can be generated corresponding to time $t_2$. In an example, the cyclic motion model can be evaluated at a time corresponding to $t_1$, and a time corresponding to $t_2=t_1+\square$. The variable, $\square$, can represent a specified latency, such as between a time corresponding to an earlier image acquisition at time $t_1$, and a scheduled upcoming therapy delivery at $t_2$.

In one approach, the cyclic motion model 500 can represent an absolute position of a feature of interest, such as a centroid of a target locus corresponding to a tumor or an organ, and the value of the cyclic motion model evaluated at time $t_2$ can be used directly as the predicted feature location at the time of therapy delivery. However, such an approach can have drawbacks, such as leading to inaccurate motion prediction if the patient is repositioned or is unable to be positioned in the same manner as when the imaging information was first acquired and used to develop the cyclic motion model. By contrast, a difference in the values of the cyclic motion model can be used to estimate a relative displacement of an imaging feature, and such a relative displacement can be used to adjust the location of the imaging feature to determine a predicted feature location at a later time, particularly over short time scales where the latency—is relatively small with respect to the overall cycle length. Accordingly, motion prediction performed using a change in feature position derived from a cyclic motion model can be insensitive, at least to a first order, to variations in target motion between the absolute position predicted by the model and the actual target position observed using imaging.

As an illustrative example, a difference between values of the cyclic motion model can be determined, such as can be represented by $f(t_1+\square)-f(t_1)$. Such a determined difference can then be used to adjust a feature location obtained from the imaging information. For example, if an imaging feature location of an acquired image corresponding to time $t_1$ is represented by $I_f(t_1)$, then the predicted feature location at time $t_2$ can be represented by $\hat{I}_f(t_2)=I_f(t_1)+[(t_1+\square)]$. In this manner, the cyclic motion model need not accurately predict a feature location in an absolute sense, but the cyclic motion model can provide a useful estimate of a change in the feature location (e.g., a relative spatial displacement) when the time corresponding to the image acquisition is aligned with the appropriate location in the cyclic model.

Alignment of the time corresponding to the image acquisition can include determining a time elapsed between a reference point in a physiologic cycle of a patient and a time at which an image is acquired. For example, a cycle phase can range from a t-value of 0 to T, where T can be the total cycle duration, such as period corresponding to a breathing cycle. A fraction of the total cycle duration (e.g., a percentage) can be determined using an expression, phase=(100t)/T. In such an expression, phase can represent a phase-percentage of the cycle at a cycle phase corresponding to time t. T can be presented in units of time (e.g., seconds or milliseconds). T can be empirically determined, such as by averaging a duration between one or more reference points or using one or more other techniques to determine a central tendency of a series of cycle duration values. In an illustrative example relating to respiration, use of cycle reference points can include measuring a series of durations between end-of-expiration (EOE) or end-of-inspiration (EOI) over one or more breathing cycles to estimate T.

Use of "phase" rather than an absolute time can allow use of a cyclic motion model that is at least somewhat scale invariant over the time dimension because such a phase is generally dimensionless. For example, an actual breathing cycle period of a patient will generally vary in absolute duration from cycle-to-cycle. Use of phase to describe an acquisition time of an image relative to a reference point along the cycle allows alignment of a phase corresponding to the acquisition time with the appropriate location along the cyclic motion model, where the phase expresses a percentage of the total cycle length, even if the absolute cycle length corresponding to acquired imaging information differs from cycle-to-cycle.

The cyclic motion model can be described in three dimensions as shown illustratively below. A feature, such as centroid location, can be extracted from an earlier-acquired image acquired at time $t_1$, where the time $t_1$ is determined by aligning the earlier-acquired image with the appropriate location (phase) along the cycle. The extracted centroid location can be represented in three dimensions as $[x_c(t_1), y_c(t_1), z_c(t_1)]$. The cyclic motion model can be represented by three functions of time, x(t), y(t), and z(t). Accordingly, in three dimensions, a predicted target locus at time $t_2$ can be determined as follows:

$$\hat{x}(t_2)=\hat{x}(t_1+\square)=x_c(t_1)+[x(t_1+\square)-x(t_1)] \quad\quad [\text{EQN. 1}]$$

$$\hat{y}(t_2)=\hat{y}(t_1+\square)=y_c(t_1)+[y(t_1+\square)-y(t_1)] \quad\quad [\text{EQN. 2}]$$

$$\hat{z}(t_2)=\hat{z}(t_1+\square)=z_c(t_1)+[z(t_1+\square)-z(t_1)] \quad\quad [\text{EQN. 3}]$$

The centroid location from the earlier-acquired image can be determined using a variety of techniques. For example, a contrast between adjacent pixels or voxels in an earlier-acquired image can be used to delineate a boundary of a region such as the target locus in the earlier-acquired image. A spatial centroid location can then be determined based upon the delineated boundary. Other approaches can be used, such as including evaluating contrast between adjacent pixels or voxels to automatically segment the boundary, or using other techniques such as edge detection.

Sources of latency contributing to the latency variable, $\square\square$ can include image acquisition latency, image processing latency such as corresponding to operations including segmentation, registration, or data transfer of imaging information, radiation therapy system latency such as corresponding to computation latency in execution of a motion prediction technique, or a latency related to therapy adjustment. Such therapy adjustment can include latencies associated with of one or more of positioning of a patient platform, positioning a radiation therapy output, or configuring an aperture-defining element such as a collimator. The latency, $\square$, need not be fixed and can be measured, manually configured, or automatically determined before the estimate is performed.

As an illustrative example, a combined MR-imaging and linac system latency can be on the order of a fraction of a second, such as around 100 milliseconds, between an imaging acquisition for purposes of target location prediction, and a subsequent delivery of radiation therapy. For such a system latency, which is on the order of a fraction of a second, the target locus can be modeled as rigid. Accordingly, a change in the location of the centroid such as provided by a cyclic motion model can be applied to an earlier-identified target locus without requiring deformation of the earlier target locus. For example, the earlier target locus can be spatially translated by a displacement corresponding to the determined change in centroid location predicted by the cyclic motion model. In this manner, a predicted target locus can be provided for use in delivery of radiation therapy.

Figure 6:
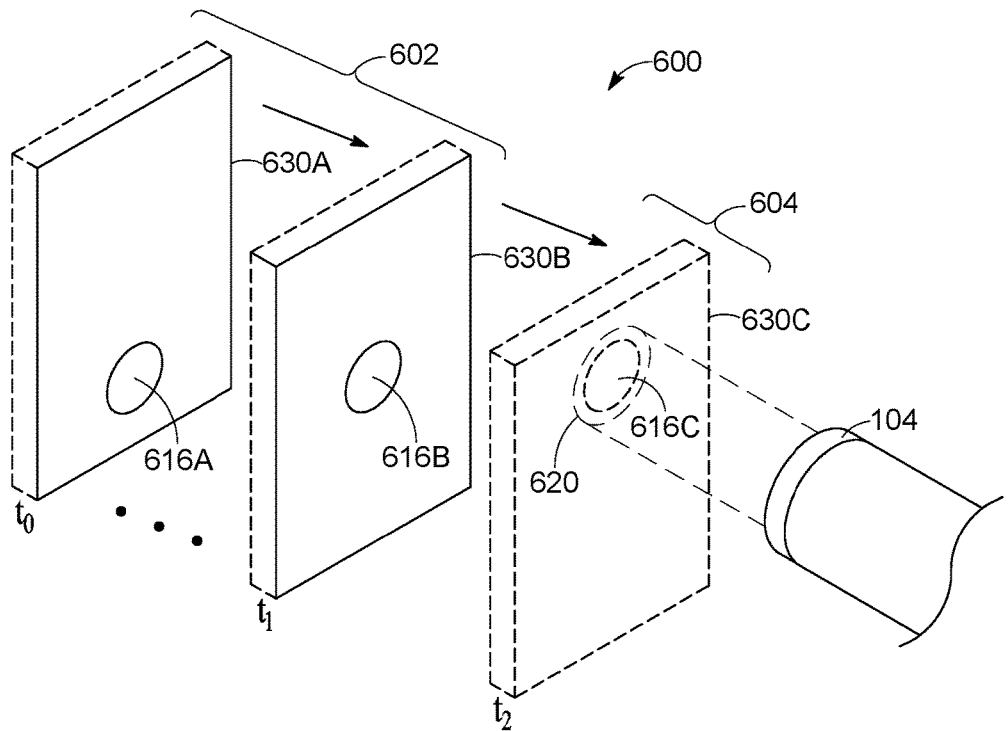
FIG. 6 illustrates an example for generating an updated therapy protocol in an adaptive manner using a cyclic motion model, and using a specified latency between image acquisition of the earlier target locus and a scheduled upcoming time of therapy delivery.

FIG. 6 illustrates an example 600 for generating an updated therapy protocol in an adaptive manner using a cyclic motion model, and using a specified latency between image acquisition of the earlier target locus and a scheduled upcoming time of therapy delivery. An earlier target locus can be identified at 602, such as using a series of acquired images. The images can include one or more of volumetric imaging information acquired over time (such to provide four-dimensional imaging information), or three-dimensional imaging information such as slices having a finite depth as shown illustratively in FIG. 6, or two dimensional imaging information, according to various illustrative examples. In an example, two dimensional imaging information or three-dimensional slices can be acquired, such as to provide a series of rapidly-acquired images over a duration of a portion or an entirety of a physiologic cycle such as a respiration cycle. At target locus 616A, such as a tumor, can be identified in a first location in an acquired image portion 630A (e.g., an imaging slice), and the target locus 616B can vary in position over time as shown in a later-acquired image portion 630B. The time-varying position of the target locus can be tracked, such as throughout the series of images acquired at 602, and a predicted target locus 616C can be determined within a region of interest 630C corresponding to a future scheduled time of therapy deliver.

The predicted target locus 616C can be provided such as by determining a time or phase of the acquisition of one or more images acquired at 602 in relation to a cycle described by a cyclic motion model as discussed above in relation to FIG. 4A, FIG. 4B, and FIG. 5, and adjusting an earlier-acquired target locus, such as the target locus 616B using a determined displacement provided by the cyclic motion model. A therapy locus 620 can then be aligned with the predicted target locus 616C for therapy delivery. In this manner, the therapy locus 620 can be adaptively aligned with a time-varying target locus such as a tumor. The therapy locus 620 refers to a region of tissue to be targeted by a radiation therapy beam provided by a radiation therapy output 104.

Figure 7:
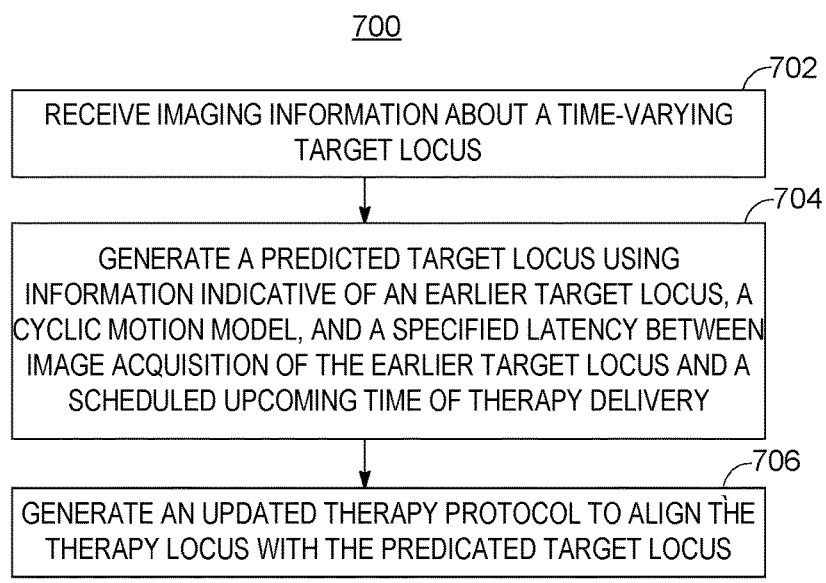
FIG. 7 is a flow chart of an exemplary method for receiving imaging information about a time-varying target locus and generating an updated therapy protocol to align a therapy locus with a predicted target locus.

FIG. 7 is a flow chart of an exemplary method 700 for receiving imaging information at 702. The imaging information can include information extracted from one or more images, the information indicative of a time-varying target locus, such as a tumor, an organ, or a portion of a tumor or organ. The target locus can represent a region of tissue within patient to be targeted by radiation therapy. At 704, a predicted target locus can be generated, such as corresponding to a scheduled upcoming time of therapy delivery. For example, the predicted target locus can be determined using information indicative of an earlier target locus and a cyclic motion model, as shown and described in examples mentioned elsewhere in this document.

The time of the scheduled upcoming therapy delivery corresponding to the predicted target locus can be determined at least in part using information about a specified latency between a time of an image acquisition of the earlier target locus and the scheduled upcoming time of therapy delivery. At 706, an updated therapy protocol can be generated, such as including aligning a radiation therapy locus with the predicted target locus. In this manner, the therapy locus of delivered radiation therapy is aligned with the moving target locus.

Figure 8:
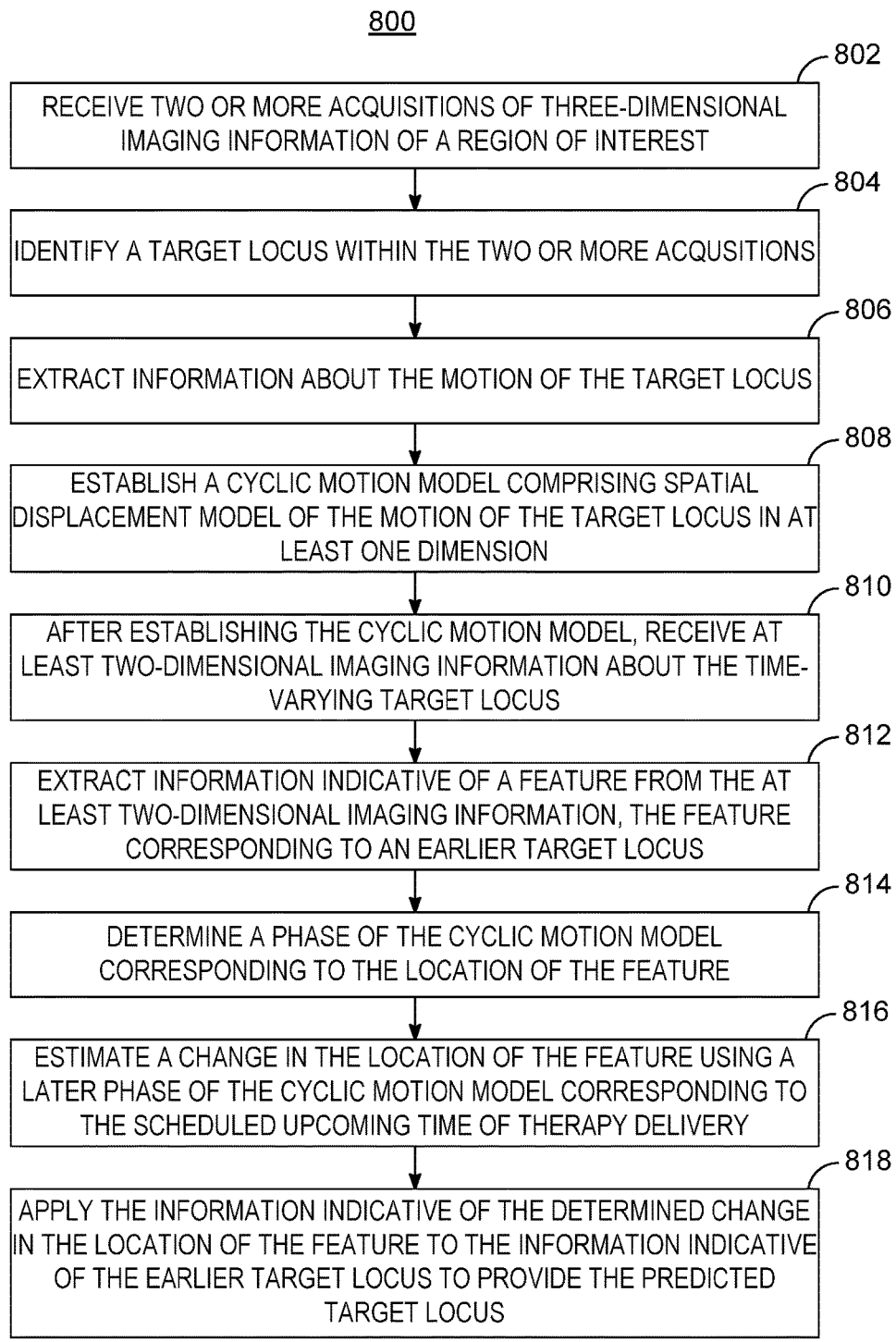
FIG. 8 is a flow chart of an exemplary method for establishing a cyclic motion model, and providing a predicted target locus using the cyclic motion model.

FIG. 8 is a flow chart of an exemplary method 800. At 802, two or more acquisitions of imaging information from a region of interest are received. For example, at 802 the acquisitions can include receiving imaging information corresponding to two or more acquisitions of three-dimensional imaging information, such as acquired using one or more of an MR imaging or CT imaging technique. At 804, a target locus can be identified within the imaging information corresponding to the two or more acquisitions. For example, the target locus can be identified through a segmentation technique as mentioned in relation to other examples described in this document.

At 806, information about a motion of the target locus can be extracted. Such information can include a spatial location of one or more features corresponding to the target locus, such as an edge or a centroid location. A change in location of the feature across the two or more image acquisitions can be determined. In response, at 808, a cyclic motion model can be established, such as comprising a spatial displacement model of the motion of the target locus in at least one dimension, such as a function of time or phase. In an example, the acquired imaging information and extracted information about the motion of the target locus can span several cycles, such as several physiologic cycles. As an illustration, imaging information can be obtained at 802 corresponding to one or more complete respiration cycles, and the cyclic motion model established at 808 can include aggregating information obtained from the obtained information into a composite, using averaging or other techniques. The series of operations at 802, 804, 806, and 808 can be performed "offline," such as well in advance of a scheduled radiation therapy treatment session (e.g., days or weeks before treatment). Alternatively, or in addition, the series of operations at 802, 804, 806, and 808 can be performed the same day as a scheduled radiation therapy treatment session, such as hours or minutes beforehand.

At 810, after establishing the cyclic motion model, imaging information can be received about the time varying target locus. For example, acquisition of images for use at 810 can be performed contemporaneously with therapy delivery, such as within seconds or even fractions of seconds before a scheduled instance of radiation therapy delivery. At 812, information indicative of a feature corresponding to an earlier target locus can be extracted from the imaging information received at 810. As shown and described elsewhere in this document, the feature can include a centroid, an edge, an indicium corresponding to an external or implantable seed, or an MR navigator echo, as illustrative examples. At 814, a phase of a cyclic motion model corresponding to the location of the feature can be determined. At 816, a change in the location of the feature can be estimated using a later phase of the cyclic motion model corresponding to the scheduled upcoming time of therapy delivery. At 818, the information determined at 816 regarding the change in location of the feature can be applied to the information indicative of the earlier target locus to provide the predicted target locus. In this manner, the therapy locus is adaptively aligned with the predicted target locus to one or more of (a) better align the radiation beam with a tissue target such as a tumor for treatment and (b) avoid or minimize damage to tissue or organs adjacent to the tissue target.

An imaging modality (e.g., MR, CT, PET, SPECT) or imaging representation (e.g., one-dimensional, two-dimensional, three-dimensional) used for establishing the cyclic motion model need not be the same as the imaging modality or representation used for extracting the information indicative of the feature, corresponding to the earlier target locus. For example, detailed high-resolution imaging information in three dimensions may be used for developing the cyclic motion model, in an "offline" fashion. Then, just before or during a radiation therapy delivery, imaging information may be acquired using a higher-speed technique, such as including higher frame rate or a shorter acquisition latency as compared to the imaging approach used for developing the cyclic motion model. In this sense, the image acquisitions corresponding to imaging information received at 810 can be referred to as occurring in "real time" relative to therapy delivery, even though such imaging need not be acquired literally simultaneously during application of the therapy beam.

Finite-Differences Based Prediction

In addition to the above-described prediction using cyclic model, other predication techniques can be used, such as non-model-based prediction techniques. In this section, embodiments of finite differences-based motion prediction techniques are described. The techniques described below in this section can be implemented in whole or in part using, or can use, the medical systems described above in relation to one or more of FIG. 1A, FIG. 1B, FIG. 1C, FIG. 2, FIG. 3A, or FIG. 3B. The examples described in this and next sections relate to the prediction of future values of a quasiperiodic physiologic signal, also referred to herein as a physiologic signal, reflecting the quasiperiodic motion of a certain region or organ in a human body, such as a respiratory signal reflecting the quasiperiodic motion of lungs. As indicated above, such a quasiperiodic motion can affect the locus of a target. Therefore, the predicted future values of the quasiperiodic physiologic signal can be used to, for example, update a therapy protocol of a therapy generator that generates a therapy beam to be directed to a locus within a therapy recipient, i.e., a patient. As another example, the predicted future values of the quasiperiodic physiologic signal can be used to align an imaging system with a locus on a target, such as a patient for whom the image is taken.

In general, the physiologic signal can be a multivariate signal, i.e., can vary in multiple dimensions, such as in three dimensions, and thus is a vector. In some scenario, the physiologic signal includes variation in only one dimension and thus is a scalar. In the present disclosure, the physiologic signal is represented generally as a vector form, x(t), but it is to be understood that the physiologic signal can be a scalar. To simplify discussion, in the examples described in this and next sections, the parameter t, although representing time, takes index values, such as 0, 1, 2, . . . , instead of absolute time values, and thus is also referred to herein as a "time index" or a "time step." The actual time value between two time steps may depend on the instrument that measures the physiologic signal.

According to the present disclosure, finite differences of the physiologic signal are used as the regular variable and a first difference between a current value of the physiologic signal at a time t and a future value of the physiologic signal at a future time t+δ, i.e., x(t+δ), is used as the target variable. That is, the first difference, i.e., the target variable, y(t), for time t in the finite-differences-based motion prediction described in this section is defined as:

$$y(t)=x(t+\delta)-x(t) \qquad [\text{EQN. 4}]$$

which is also referred to herein as a "difference value." The difference value is indicative of a difference between a future time t+δ and a current time t. In the present disclosure, the parameter δ is also referred to as a "prediction horizon," which represents a time span from the current time to the future time for which the prediction is conducted. Like the time t, the prediction horizon δ can also take an index value or an absolute time value. In the examples discussed in this and next sections, to simplify discussion, the prediction horizon δ also takes an index value.

According to the disclosure, a set of derivatives of the physiologic signal evaluated at time t, from the first order to higher orders (x'(t), x''(t), x'''(t), . . . , can be used as the regular variable. In practice, however, finite differences of the physiologic signal at time t are used to approximate the derivatives since finite differences past time t are not known and the physiologic signal is discrete, i.e., sampled at discrete times. The set of finite differences of the physiologic signal at time t, i.e., the regular variable, can be represented by a differences signal d(t,p,o), defined as follows:

$$d(t, p, o) = \begin{pmatrix} x(t) - x(t - p_1) \\ x(t) - 2x(t - p_1) + x(t - (p_1 + p_2)) \\ x(t) - 3x(t - p_1) + 3x(t - (p_1 + p_2)) - x(t - (p_1 + p_2 + p_3)) \\ \vdots \\ x(t) + \sum_{j=1}^{o} (-1)^j \binom{o}{j} x\left(t - \sum_{h=1}^{j} p_h\right) \end{pmatrix} \qquad [\text{EQN. 5}]$$

where $$\binom{o}{j} = \frac{o!}{j!(o-j)!} \qquad [\text{EQN. 6}]$$

and the parameter o represents the order of differences included in the differences signal and thus controls the size of the differences signal. The parameter o is also referred to herein as a "differences signal scale." The value of the differences signal scale o can depend on various factors, such as the physiologic signal, the application, and the prediction horizon δ.

Thus, according to the present disclosure, in addition to the first order finite difference, at least one high-order finite difference, i.e., a finite difference of the second or higher order, are used for the prediction. In EQN. 5, four finite differences, i.e., the first, second, third, and o-th order finite differences are shown. However, it is to be understood that EQN. 5 is a general representation of the differences signal, which is not limited to the particular finite differences in EQN. 5. For example, the differences signal can include the first and second order finite differences of the physiologic signal. In some embodiments, the differences signal includes the first, second, and third, or additionally higher-order finite differences of the physiologic signal. With the high-order finite differences used in the prediction according to the present disclosure, future values of the physiologic signal can be predicted more accurately.

The vector $p=[p_1, p_2, \ldots, p_o]^T$ in EQN. 5 is also referred to herein as a "step-size vector." Each component in this vector controls the step-size used for taking the finite difference of a corresponding order. For example, $p_1$ represents the step size for taking the first order finite difference of the physiologic signal and is thus also referred to herein as a "first order step size," $p_2$ represents the step size for taking the second order finite difference of the physiologic signal and is thus also referred to herein as a "second order step size," and $p_o$ represents the step size for taking the o-th order finite difference of the physiologic signal and is thus also referred to herein as an "o-th order step size." The step sizes $p_1, p_2, \ldots, p_o$ are chosen based on various factors such as the characteristics of the physiologic signal, the application, and the measurement of the physiologic signal. In some embodiments, the step sizes $p_1, p_2, \ldots, p_o$ can depend on the value of the prediction horizon δ. According to the present disclosure, $p_1, p_2, \ldots, p_o$ can be the same as or different from each other. For example, $p_1, p_2, \ldots, p_o$ can all equal 1.

The regular/target variable pair $\langle d(t,p,o),y(t) \rangle$ defined above can be used with any suitable prediction algorithms to predict the future values of the physiologic signal. In the present disclosure, the prediction algorithm used with the variable pair $\langle d(t,p,o),y(t) \rangle$ to predict future values is also referred to herein as a predictor. Various prediction algorithms can be used in conjunction with the variable pair consistent with embodiments of the present disclosure. The prediction algorithm may be, for example, support vector regression, non-parametric probability-based methods such as kernel density estimation, or linear regression.

Before the above-described predictor can be used to predict future values of the physiologic signal, the predictor would be trained to determine proper predictor parameter values. Consistent with the present disclosure, historical, measured values of the physiologic signal, $\{x(k):k=0, 1, \ldots, n\}$, can be used to train the predictor. Accordingly, the disclosed methods may be suitable to work on the fly, and adaptive to baseline shifts. Here, k takes an index value and represents the time at which a measurement is conducted and a value of the physiologic signal is obtained. In this example, a total of n+1 measurements are conducted, each of which corresponds to one-time index k.

As discussed above, for a certain time k', a future value of the physiologic signal at a future time k'+δ can be predicted. To train the predictor, both the regular variable, i.e., the differences signal, and the target variable, i.e., the difference value, need to be known. Therefore, in this example, the highest value for k' can be n−δ. This is because, for example, if k' equals n−δ+1, then the future time corresponding to time k' is n+1, but there is no measured data for time point n+1, and thus no difference value y(k') can be calculated for time k'=n−δ+1 for the training purpose. Further, according to EQN. 5, to calculate the differences signal for time k', data points in the range from time $(k'-\Sigma_{h=1}^{o} p_h)$ to time k' are needed. Thus, since in this example the lowest time index k is 0, the lowest value for k' should be $\Sigma_{h=1}^{o} p_h$. Therefore, in this example, the value of k' can be $\Sigma_{h=1}^{o} p_h, \Sigma_{h=1}^{o} p_h+1, \ldots, n-\delta$.

For example, assume 20 data points of the physiologic signal are measured, i.e., a data set $\{x(k):k=0, 1, \ldots 19\}$ is obtained. Further assume that the differences signal includes three finite differences, i.e., o=3 and $p=[p_1, p_2, p_3]^T$ with $p_1=p_2=p_3=1$, and that δ=2. Then the value of time k' can be 3, 4, . . . , 17.

With the values of k' determined as described above, a training variable pair $\langle d(k',p,o),y(k') \rangle$ can be calculated for each k', with $k'=\Sigma_{h=1}^{o} p_h, \Sigma_{h=1}^{o} p_h+1, \ldots, n-\delta$. The obtained training variable pairs $\langle d(k',p,o),y(k') \rangle$ can then be used to train the predictor to obtain proper predictor parameter values.

After the predictor is trained, the predictor can be used to predict a future value of the physiologic signal based on any current value of the physiologic signal at a current time $t_c$. First, for the current time $t_c$, the differences signal $d(t_c,p,o)$ is calculated using EQN. 5. The calculated differences signal $d(t_c,p,o)$ is then substituted into the predictor as the regular variable to predict the target variable, i.e., the difference value $\hat{y}(t_c)$, which is then used to calculate the predicted value of the physiologic signal at the future time $t_c+\delta$ according to $\hat{x}(t_c+\delta)=\hat{y}(t_c)+x(t_c)$ (the hat symbol "^" above symbols x and y indicates they are predicted values). As discussed above, the predicted future value $\hat{x}(t_c+\delta)$ can be used to, for example, predict a target locus on a therapy recipient of a therapy delivery system and to update a therapy protocol used by a therapy generator of the therapy delivery system, such as including aligning a radiation therapy locus with the predicted target locus.

Figure 9:
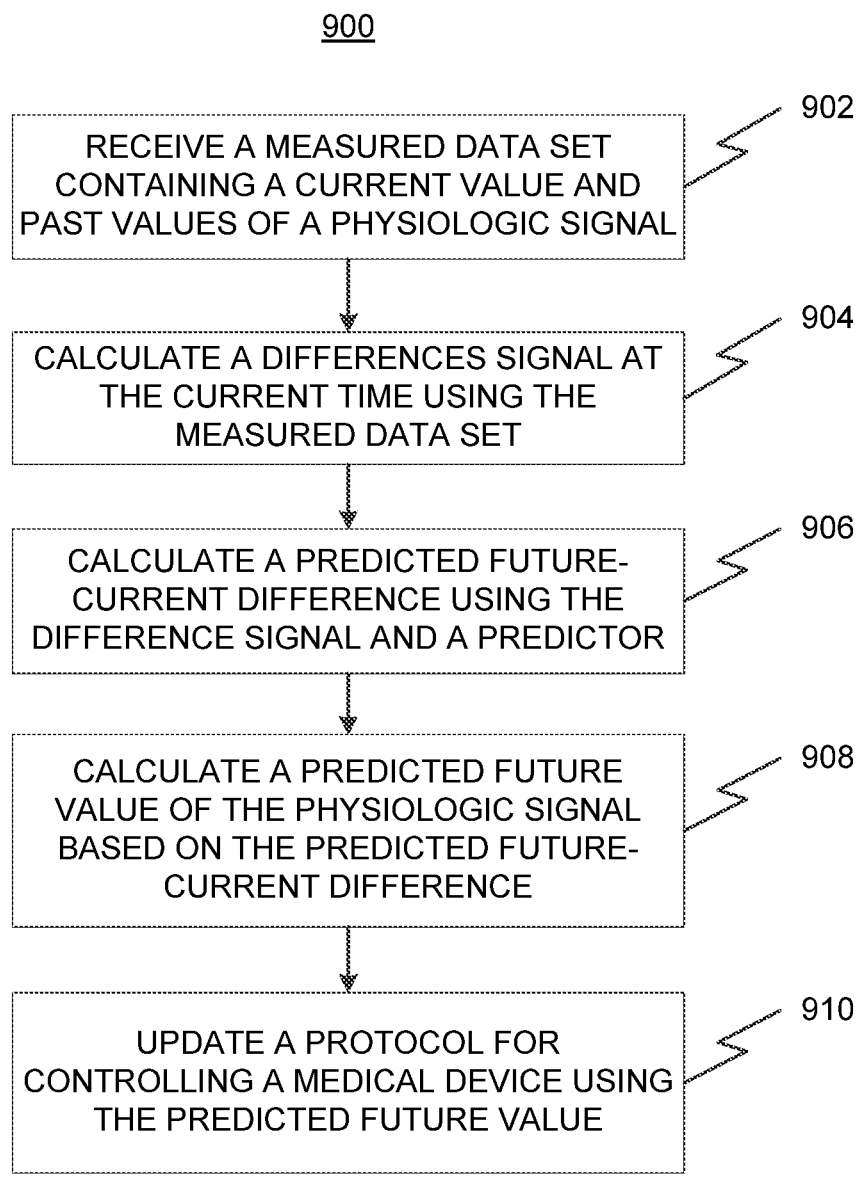
FIG. 9 is a flow chart of an exemplary method for signal prediction using finite differences according to an exemplary embodiment.

FIG. 9 shows a flow chart of an exemplary method 900 consistent with embodiments of the present disclosure for predicting a future value of a physiologic signal. As shown in FIG. 9, at 902, a measured data set containing a current value of the physiologic signal at a current time and past values of the physiologic signal at times before the current time is received. The physiologic signal can be, for example, a respiratory signal reflecting the quasiperiodic motion of the lungs of a target, such as a therapy recipient. At 904, a differences signal at the current time is calculated using the measured data set. The calculation can be conducted using, for example, EQN. 5. At 906, a predicted difference value is calculated by substituting the differences signal into a predictor. At 908, a predicted future value of the physiologic signal is calculated based on the predicted difference value and the current value of the physiologic signal. At 910, the predicted future value of the physiologic signal is used to update a protocol for controlling a medical device. The medical device can be, for example, an imaging system for taking images of, or a therapy delivery system for delivering therapy to, an object, such as a patient. The protocol can be used to, for example, control the alignment of the medical device. Thus, the predicted future value can be used to, for example, align the imaging system or a therapy generator of the therapy delivery system with a target locus on the object. For example, the predicted future value can be used to update a therapy protocol of the therapy generator of the therapy delivery system, where the therapy protocol is used to control the therapy generator to direct the therapy beam.

Figure 10:
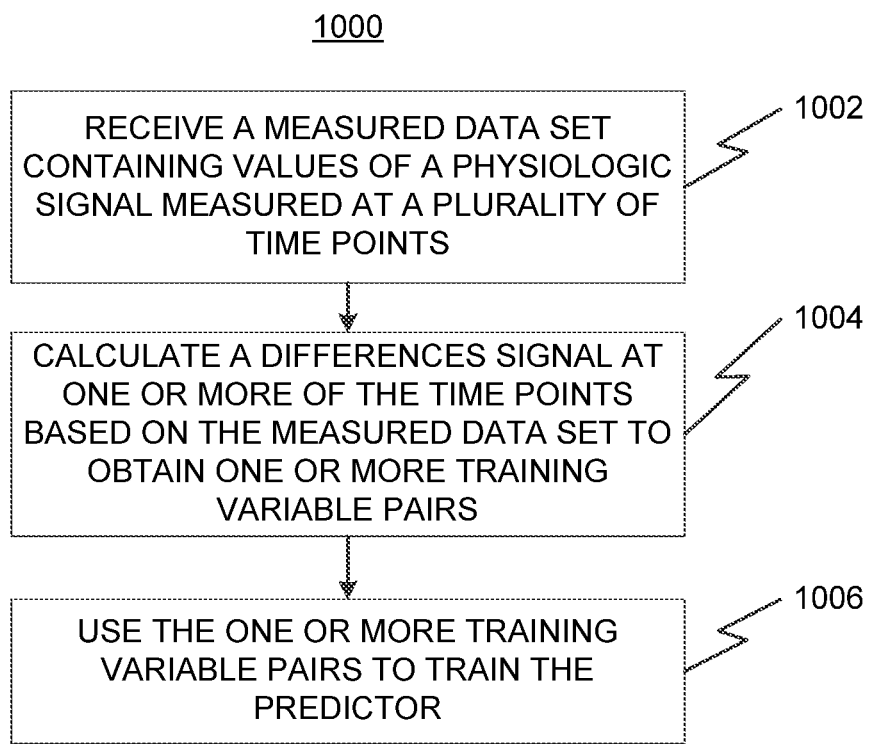
FIG. 10 is a flow chart of an exemplary method for training a predictor using finite differences according to an exemplary embodiment.

FIG. 10 shows a flow chart of an exemplary method 1000 consistent with embodiments of the present disclosure for training a predictor used for predicting future values of a physiologic signal. As shown in FIG. 10, at 1002, a measured data set containing values of the physiologic signal measured at a plurality of time points is received. At 1004, a differences signal at one or more of the time points is calculated based on the measured data set, to obtain one or more training variable pairs each containing the calculated differences signal at the time point and a difference value corresponding to the time point. Hereinafter, a differences signal calculated during training is also referred to as a "training differences signal" and a difference value calculated during training is also referred to as a "training difference value." At 1006, the one or more training variable pairs are used to train the predictor to obtain proper parameter values for the predictor.

The exemplary methods shown in FIGS. 9 and 10, although described separately above, can be combined together consistent with the present disclosure. For example, the exemplary method 1000 can be conducted first to train a predictor using historical measured values of the physiologic signal, and then the trained predictor is used to predict the future values of the physiologic signal according to the exemplary method 900. Consistent with some embodiments, the predictor may be re-trained one or more times during any suitable point of method 900 to adapt to drift in the breathing behavior. The retraining may be performed on the fly and provide updated parameter values for the predictor. A predictor so adaptively trained on the fly can better compensate for the baseline shifts.

Using the methods consistent with the present application, the prediction performance of each prediction algorithm can be improved as compared to the results without using the finite differences, and is significantly improved as compared to the results without any prediction.

Prediction Based on Model Regression

Both model-based methods, such as Kalman filter, and model-free methods, such as normalized least mean-square filter and regression methods, can be used to predict future values of a physiologic signal. Model-based methods predict the physiologic signal in a context. Therefore, in addition to the future values of the physiologic signal, the model-based methods can also predict an internal state of an anatomical structure, i.e., the source of the quasiperiodic motion that generates the physiologic signal. For example, the anatomical structure may be a region on or an organ of a human body, such as a patient or a therapy recipient. As such, the physiologic processes of the anatomical structure can be inferred from the information about the internal state of the anatomical structure. Moreover, by knowing the internal state of the anatomical structure and its relationship with the physiologic signal, the signal can be predicted at different prediction horizons without changing the parameters of the predictor.

On the other hand, model-free methods use numerical methods to determine a mapping from a current set of measured or observed values of the physiologic signal to expected future values of the physiologic signal, and are thus more flexible towards changes in the characteristics of the physiologic signal.

In this section, motion prediction techniques based on model regression is described. The model regression methods consistent with the present disclosure apply model-free prediction methods to determine the model of the anatomical structure, and thus benefit from the advantages of both the model-based and model-free prediction methods. The techniques described below in this section can be implemented in whole or in part using, or can use, the medical systems described above in relation to one or more of FIG. 1A, FIG. 1B, FIG. 1C, FIG. 2, FIG. 3A, or FIG. 3B.

As discussed above, the physiologic signal x(t) is a function of time. In this section, x(t) is also denoted as:

$$x(t) = f(.)(t) \qquad [EQN.\ 7]$$

where $f(.)$ denotes a functional representation that can be used to calculate values, such as future values, of the physiologic signal. The functional representation takes time t as input and output the values of the physiologic signal at time t, i.e., x(t). The functional representation can be determined according to the model regression methods of the present disclosure. Specifically, the relationship between the functional representation of the physiologic signal x(t), i.e., $f(.)$, and the internal state at time t can be represented as follows:

$$f(.) = f(s_t)(t) \qquad [EQN.\ 8]$$

where $s_t$ denotes a state representation representing specific results of the internal state s(t) of the anatomical structure at time t, and $f(s_t)$, hereinafter also referred to as a "mapping function," denotes a mapping from the state space to the functional representation of the physiologic signal, $f(.)$. The state representation $s_t$ may be a vector or a scalar. When the state representation $s_t$ is a vector, it is also referred to as a "state vector." The internal state s(t), and thus the state representation $s_t$, are particular to the model used, and can be different for different models. Thus, not only the physiologic signal x(t) is a function of time, the functional representation $f(.)$ used to calculate the physiologic signal x(t) is also a function of time and depends on the state representation $s_t$. That is, the functional representation $f(.)$ can change with time.

Therefore, according to the present disclosure, the particular type and form of the functional representation $f(.)$ at time t depend on the internal state s(t) and are determined by the state representation $s_t$ at time t according to the mapping function $f(s_t)$. For example, depending on the internal state, the functional representation $f(.)$ can be a linear function, a quadratic function, or a cubic function, with a particular set of coefficients. The set of coefficients forms the state representation $s_t$. Therefore, if the mapping function $f(s_t)$ and the state representation $s_t$ for a time point t are known, the functional representation $f(.)$ can be determined, and thus the value of the physiologic signal can be calculated according to the determined functional representation $f(.)$. Further, at different time points, the functional representation $f(.)$ used to calculate the physiologic signal x(t) may be different. For example, for the same physiologic signal, the functional representation $f(.)$ may be a quadratic function for one state but a cubic function for another state.

For example, assume the physiologic signal is a univariate signal and can be represented as x(t), and the functional representation $f(.)$ at time t is a cubic polynomial defined by four parameters $a_1(t)$, $a_2(t)$, $a_3(t)$, and $a_4(t)$, which form the state representation $s_t = [a_1(t), a_2(t), a_3(t), a_4(t)]^T$. Hence the physiologic signal x(t) in this example can be calculated by: $x(t)=a_1(t)+a_2(t)t+a_3(t)t^2+a_4(t)t^3$. In general, when the physiologic signal is a multivariate signal, each of $a_1(t)$, $a_2(t)$, $a_3(t)$, and $a_4(t)$ can also be multivariate.

According to the present disclosure, once the functional representation $f(.)$ is determined according to EQN. 8, the predicted future value of the physiologic signal at a future time $t+\delta$, i.e., $x(t+\delta)$, can be calculated using EQN. 7 and historical measured values of the physiologic signal. The set of historical measured values of the physiologic signal includes the measured values for a time range starting from a time in the past, referred to herein as time $t_0$, to a current time $t_c$. This time range is also referred to herein as a "measurement time range." The process for calculating the future value of the physiologic signal using EQN. 7, EQN. 8, and the historical measured values is described below.

For each of one or more of the time points in the measurement time range, the state representation $s_t$ is estimated based on the set of historical measured values. For example, the state representation $s_t$ for a particular time point $t_1$ can be determined based on the measured values of the physiologic signal at the time point $t_1$ and one or more previous time points. In some embodiments, the state representation $s_t$ is estimated for each of the time points in the measurement time range. According to the present disclosure, the state representation $s_t$ can be estimated using various appropriate methods, such as a regression method. An estimated state representation is also referred to herein as a historical state representation, and the set of estimated state representations is also referred to herein as a state representation history.

Based on the state representation history, a predicted state representation $\hat{s}_{t+\delta}$ at the future time $t+\delta$ can be calculated using an appropriate prediction algorithm. In some embodiments, a regression method, such as kernel density estimation, support vector regression, or linear regression, can be used to calculate the predicted state representation $\hat{s}_{t+\delta}$. In some embodiments, an adaptive filtering scheme, such as normalized linear mean-square (nLMS) filter, can be used to calculate the predicted state representation $\hat{s}_{t+\delta}$.

Based on the predicted state representation $\hat{s}_{t+\delta}$, a predicted functional representation $f(.)$ at the future time $t+\delta$ can be determined by substituting the state representation $\hat{s}_{t+\delta}$ into EQN. 8. Further, the predicted future value $\hat{x}(t+\delta)$ can be calculated by substituting the future time $t+\delta$ into EQN. 7 with the predicted functional representation, i.e., $\hat{x}(t+\delta)=f(.)(t+\delta)$.

Before the above-described predictor can be used to predict future values of the physiologic signal, it may need to be trained to determine the proper correlation between the functional representation $f(.)$ and the state representation $s_t$, i.e., to determine the proper mapping function $f(s_t)$. Consistent with the present disclosure, historical measured values of the physiologic signal can be used to train the predictor. The set of historical measured values of the physiologic signal used for training the predictor can be the same as or different from the set of historical measured values used to calculate the predicted state representation $\hat{s}_{t+\delta}$. In the present disclosure, the set of historical measured values of the physiologic signal used for training the predictor is also referred to as a "training data set."

With the given training data set, a state representation $s_t$ for each of the time points in the training data set can be estimated using, for example, a regression method, such as kernel density estimation. An estimated state representation $s_t$ based on the training data set is also referred to herein as a training state representation, and the set of training state representations is also referred to herein as a training state representation set. As an example, the predictor can be trained to find the proper mapping function $f(s_t)$ using one or more training pairs, each of which may include the estimated state representation at a particular time $t'$, i.e., $s_{t'}$, and the value of physiologic signal at time $t'+\delta$, i.e., $x(t'+\delta)$. Various appropriate methods can be used for the training purpose. For example, a regression method, such as kernel density estimation, can be used for the training purpose.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, examples in which only those elements shown or described are provided. Moreover, any combination or permutation of those elements shown or described (or one or more aspects thereof), either with respect to a particular example (or one or more aspects thereof), or with respect to other examples (or one or more aspects thereof) shown or described herein are within the scope of the present disclosure.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A medical system, comprising:
a medical device, configured to be controlled according to a control protocol; and
a controller configured to:
receive a measured data set containing a current value at a current time and past values at past times of a physiologic signal measured on a recipient;
calculate a difference signal at the current time based on the measured data set, the difference signal including a first order finite difference of the physiologic signal at the current time and a second order finite difference of the physiologic signal at the current time, the first and second order finite differences respectively corresponding to first and second derivatives;
predict a difference value using the difference signal and a prediction algorithm, the difference value being a difference between a predicted future value of the physiologic signal at a future time and the current value;
calculate the predicted future value based on the difference value and the current value; and
update the control protocol according to the predicted future value.

2. The medical system of claim 1, wherein the difference signal further includes one or more higher order finite differences of the physiologic signal at the current time, the one or more higher order finite differences having an order higher than the second order finite difference.

3. The medical system of claim 2, wherein a highest order of the one or more higher order finite differences is determined based on at least one of the physiologic signal, or a time difference between the future time and the current time.

4. The medical system of claim 1, wherein the controller is configured to calculate the first order finite difference using a first step size and the second order finite difference using a second step size.

5. The medical system of claim 4, wherein the first step size equals to the second step size.

6. The medical system of claim 4, wherein the first step size differs from the second step size.

7. The medical system of claim 4, wherein the first step size and the second step size are determined based on at least one of characteristics of the physiologic signal, an application of the medical system, a measurement of the physiologic signal, or a time difference between the future time and the current time.

8. The medical system of claim 1, wherein the prediction algorithm includes one of kernel density estimation, support vector regression with scaling, or random forest regression.

9. The medical system of claim 1, wherein:
the prediction algorithm is trained using a training variable pair comprising a training difference signal and a training difference value;
the training difference signal represents a finite difference of the physiologic signal at a first time point that precedes the current time; and
the training difference value represents a difference between a second value of the physiologic signal at a second time point, that follows the first time point, and a first value of the physiologic signal at the first time point, the second time point preceding the current time.

10. The medical system of claim 1, wherein the controller is further configured to:
receive historical measured values of the physiologic signal measured at a plurality of time points before predicting the difference value;
calculate a training difference signal at one or more time points based on the historical measured values, to obtain one or more training variable pairs each containing one training difference signal and a corresponding training difference value; and
train the prediction algorithm using the one or more training variable pairs.

11. A method for controlling a medical device, comprising:
receiving a measured data set containing a current value at a current time and past values at past times of a physiologic signal measured on a recipient;
calculating a difference signal at the current time based on the measured data set, the difference signal including a first order finite difference of the physiologic signal at the current time and a second order finite difference of the physiologic signal at the current time, the first and second order finite differences respectively corresponding to first and second derivatives;
predicting a difference value using the difference signal and a prediction algorithm, the difference value being a difference between a predicted future value of the physiologic signal at a future time and the current value;
calculating the predicted future value based on the difference value and the current value; and
updating a control protocol of the medical device according to the predicted future value.

12. The method of claim 11, wherein the difference signal further includes one or more higher order finite differences of the physiologic signal at the current time, the one or more higher order finite differences having an order higher than the second order finite difference.

13. The method of claim 12, further comprising:
determining a highest order of the one or more higher order finite differences based on at least one of the physiologic signal, an application of the medical device, or a time difference between the future time and the current time.

14. The method of claim 11, wherein calculating the difference signal includes calculating the first order finite difference using a first step size and calculating the second order finite difference using a second step size.

15. The method of claim 14, wherein the first step size equals to the second step size.

16. The method of claim 14, wherein the first step size differs from the second step size.

17. The method of claim 14, further comprising:
determining the first step size and the second step size based on at least one of characteristics of the physiologic signal, an application of the medical device, a measurement of the physiologic signal, or a time difference between the future time and the current time.

18. The method of claim 11, wherein predicting the difference value uses one of kernel density estimation, support vector regression with scaling, or random forest regression.

19. The method of claim 11, wherein:
the prediction algorithm is trained using a training variable pair comprising a training difference signal and a training difference value;
the training difference signal represents a finite difference of the physiologic signal at a first time point that precedes the current time; and
the training difference value represents a difference between a second value of the physiologic signal at a second time point, that follows the first time point, and a first value of the physiologic signal at the first time point, the second time point preceding the current time.

20. The method of claim 11, further comprising training the prediction algorithm, wherein training the prediction algorithm includes:
receiving historical measured values of the physiologic signal measured at a plurality of time points before predicting the difference value;
calculating a training difference signal at one or more of the time points based on the historical measured values, to obtain one or more training variable pairs each containing one training difference signal and a corresponding training difference value; and
training the prediction algorithm using the one or more training variable pairs to obtain parameter values of the prediction algorithm.

* * * * *